United States Patent [19]
Rihel

[11] Patent Number: 5,275,559
[45] Date of Patent: Jan. 4, 1994

[54] METHOD OF USING A TRANSPARENT DISK DURING A DENTAL PROCEDURE

[76] Inventor: Vicki L. Rihel, 818 S. Westwood, Suite 209, Mesa, Ariz. 85210

[21] Appl. No.: 969,002

[22] Filed: Oct. 30, 1992

[51] Int. Cl.$^5$ .............................................. A61C 1/16
[52] U.S. Cl. .............................................. 433/116
[58] Field of Search ............... 433/31, 80, 116, 93, 433/136; 604/77, 268

[56] References Cited

U.S. PATENT DOCUMENTS

| | | | |
|---|---|---|---|
| 4,424,036 | 1/1984 | Lokken | 433/116 |
| 4,611,992 | 9/1986 | Lokken | 433/80 |
| 5,067,899 | 11/1991 | Paschal | 433/116 |

*Primary Examiner*—Cary E. O'Connor
*Attorney, Agent, or Firm*—Donald J. Lisa

[57] ABSTRACT

A thin, clear, plastic disk has a central aperture through which is inserted a resilient o-ring. The o-ring is slipped over and frictionally engages with the fitting which secures the nozzle of an air/water syringe to the syringe handle. During the performance of a dental procedure using this instrument the shield is positioned close to the mouth of the patient and blocks matter ejected from the patient's mouth by the force of the air/water spray before it can become airborne and shields the splatter from being deposited on any exposed areas of the dental professional's face, head, hair and neck. This simple, efficient technique prevents contaminating the professional with the germs, bacteria and other potentially infectious viruses of the patient, including the AIDS virus.

7 Claims, 1 Drawing Sheet

METHOD OF USING A TRANSPARENT DISK DURING A DENTAL PROCEDURE

BACKGROUND OF THE INVENTION

1. Fields Of The Invention

The present invention relates generally to the method of preventing cross contamination between a patient and a health care worker, and, more particular, to shielding the health care worker with a clear, thin, plastic disk from matter ejected from the patient's mouth during a dental procedure.

2. Discussion Of Background And Prior Art

During the performance of a dental operation it is often necessary for the dental professional to spray air or water or both into a patient's mouth. A typical operation done by a dental technician, known as, prophylaxis, is a routine, preventive procedure involving cleaning of the patients' gums and teeth which results in significant bleeding and the dislodgement of food-debris and tarter build-up which mixes with the patient's saliva. When the dental technician sprays water and/or air into the patient's mouth during the procedure, the mixture, including the water spray, is ejected from the patient's mouth toward the dental technician and presents a significant health hazard to the dental technician.

In recent years the health hazard has been significantly increased because of the HIV virus which causes AIDS and which is transmitted in the blood of an infected patient. If exposed to the bloodstream of the health care worker, this virus most likely will infect the health care worker.

In the past many devices have been provided to guard against this health hazard. The most well known devices include a paper face mask covering the mouth and nose of the health care worker which prevents inhaling fine particles and droplets of ejected matter. Also, eyeglasses act as a physical barrier. The problem with these obvious coverings is that they leave much of the head and neck area of the health care worker exposed.

A variety of prior clear, plastic face shields are known to address this "splatter" problem. These devices are available in several variations including a visor style face shield, a plastic face shield that clips to the side of the health care worker's glasses and a plastic shield which is an extension of a paper face mask to provide a see-through covering for the eye area. The deficiency with these devices still is, however, that they protect only portions of the face area and leave exposed the balance of the face and neck area of the health care worker.

For example, experience has shown that a health care worker wearing a plastic face shield of the type referred to above will often observe upon completion of the treatment of a patient the presence of little water spots at the very top of the shield. Obviously, if the spray and splatter reaches the top of the shield, which is usually in the mid-forehead area, then it certainly reaches the hair and neckline of the health care worker who may, for example, be readily infected with AIDS if an open sore is present in that area.

At the present time there is not available a product which can completely shield the health care worker from all spray and splatter ejected from a patient's mouth during routine dental operations, such as, those involving the use of an air/water syringe.

The present invention solves this problem by using a thin clear plastic disc positioned close to the patient's mouth during the procedure to effectively block ejected matter before it can become airborne or deposited on the clothing, hair or exposed skin surfaces not already covered by glasses, masks and other face shields.

SUMMARY OF THE INVENTION

Set forth below is a brief summary of the invention in order to achieve the forgoing and other benefits and advantages in accordance with the purposes of the present invention as embodied and broadly described herein.

One aspect of the invention is the method of using a transparent disk while performing a dental procedure inside a patient's mouth which includes the step of blocking with the disk matter ejected from the patient's mouth during the dental procedure thereby effectively shielding the operator from the splatter.

A further feature of this form of the invention includes positioning the disk close to the patient's mouth so that the splatter is blocked before it has a chance to become airborne, be deposited on or be inhaled by the health care worker.

In a second aspect of the invention the transparent disk is attached to the instrument used in the dental procedure. In a more particular form of this aspect of the invention, the transparent disk has a central aperture therethrough with a bushing or insert therein which is frictionally engaged with the instrument used in the procedure.

In the particular form of the invention which involves the use of an air/water syringe the syringe nozzle is inserted through the aperture and the resilient bushing is frictionally secured to the fitting which connects the nozzle to the air/water syringe handle.

The syringe spray shield of the present invention simply and efficiently blocks ejected matter close to the source before it has an opportunity to infect the health care worker and without interfering with the dental operation in any way.

DETAILED DESCRIPTION OF THE PREFERRED EMBODIMENT

Figure 1:
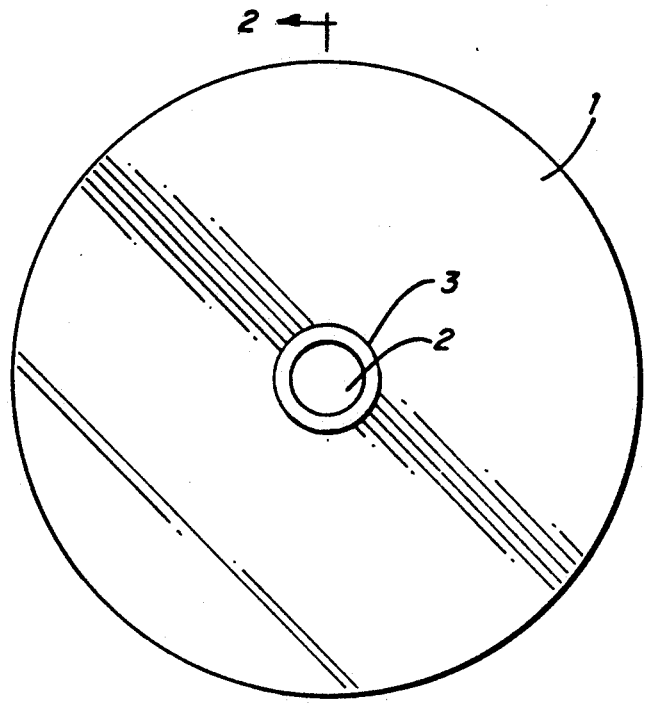
FIG. 1 is a plan view of the transparent disk of the present invention.
Figure 2:
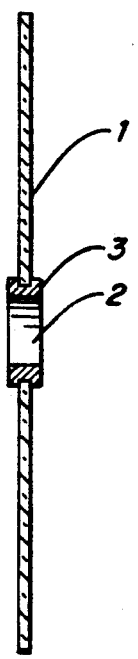
FIG. 2 is a side sectional elevational view of the transparent disk of the present invention.

As shown in FIG. 1, disk 1 is a thin, transparent, plastic disc having a central bore 2 in which is inserted insert 3.

Disk 1 is preferably a round disc. However, it may have a square or other shape, such as octagonal or the like. The plastic material is any well known plastic.

While clear plastic is preferred, so that visibility is not impaired in performing the dental operation or procedure, the invention is not avoided by the use of materials which may be translucent or lightly colored, such as light pink or yellow so long as the visibility through the disk is not substantially reduced and does not impair the ability of the operator or technician to safely and competently perform the operation or procedure.

The insert 3 is any well known bushing or o-ring which is resilient and flexible to enable the central bore of the bushing to be frictionally engaged with the instrument used in the procedure in one way or another. The bushing may be either removable, such as, a rubber o-ring snapped into place, or it may be affixed to the disk in a conventional manner.

An example of a disk is one that is 4¼" in diameter having a ⅜" bore, with a ⅜" outside diameter o-ring inserted into the disk central aperture. The o-ring is typically made of rubber and is ⅛" thick axially.

The inner bore of the o-ring is predeterminedly selected of a diameter slightly smaller than the outside diameter of the fitting 15 so that the o-ring may be frictionally engaged on the fitting as described below.

Figure 3:
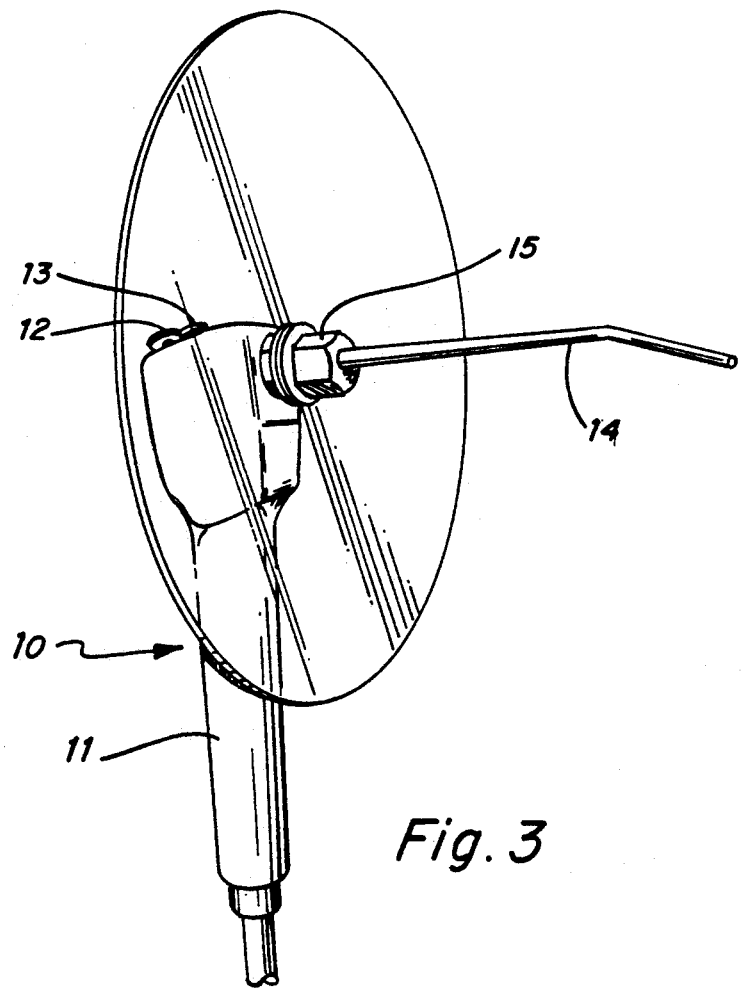
FIG. 3 is a perspective view of an air/water syringe used in a dental procedure with the transparent disk of the present invention frictionally engaged with the fitting which secures the spray nozzle to the syringe handle.

As seen in FIG. 3, an air/water syringe 10 includes a handle 11, a water button 12, an air button 13 and a nozzle 14 secured to the handle 11 by fitting 15, which has a typical hexagonal shape. The outside diameter of the fitting 15 is slightly larger than the diameter of the inner bore of the rubber o-ring 3.

In operation, the syringe spray shield of the present invention is used in the following manner.

Nozzle 14 is inserted through aperture 2 of the air/water syringe instrument until the fitting 15 is pushed all the way through so that the side edge of bushing 3 abuts the handle 11 of the syringe instrument. Because the OD of fitting 15 is larger than the ID of insert 3, disk 1 is thereby frictionally attached to and secured on the air/water syringe 10.

Other means of attachment are possible. For example, the insert 3 may be of a different variety with a pair of spaced ears or the like extending there from axially parallel to the bore and configured in a wide variety of ways to enable the insert 3 to be engaged with, attached to or secured on the handle 11 without interfering with the health worker's visibility. All of these wide varieties of attaching means are intended to be included within the scope of the present invention and are generally comprehended by the attaching step described above, which is absolutely not limited to a simple frictional engagement step.

When the operator performs the air/water spray step of the dental procedure, he inserts the nozzle 14 in or close to the patient's mouth which positions the disk 1 at or near the patient's mouth. When the air/water syringe is activated, any matter, including blood, water, saliva and food debris which may be deflected, dislodged, ejected, ricocheted, bounced, rebounded, or otherwise ejected from the patient's mouth will be efficiently and effectively blocked and shielded before it can become airborne close to the source thereby preventing splatter onto or about the exposed areas of the health worker's body. Anything from a fine mist to a forceful spray is efficiently blocked.

The disk is easily removed by simply pulling it from its frictional engagement with the fitting 15 and may be readily disposed of between patients. A replacement disk 1 is readily inserted.

While the example described above in the preferred embodiment is that of a thin, clear, plastic disk used with an air/water syringe dental instrument, this invention is intended to encompass the entire environment of shielding health care workers using instruments in dental procedures generally.

The foregoing description of a preferred embodiment and best mode of the invention known to applicant at the time of filing the application has been presented for the purposes of illustration and description. It is not intended to be exhaustive or to limit the invention to the precise form disclosed, and obviously many modifications and variations are possible in the light of the above teaching. The embodiment was chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

I claim:

1. The method of using a transparent disk while performing a dental procedure inside a patient's mouth comprising the steps of:
   frictionally attaching the disk to a dental instrument:
   positioning the disk close to the patient's mouth; and
   blocking with the disk matter ejected from the patient's mouth during the dental procedure.

2. The method of using a transparent disk while performing a dental procedure inside a patient's mouth as set forth in claim 1 wherein the disk has a central aperture and a bushing in the central aperture and the frictionally attaching step further comprises:
   engaging the bushing with the instrument.

3. The method of using a transparent disk while performing a dental procedure inside a patient's mouth as set forth in claim 2 wherein the instrument is an air/water syringe having a fitting and nozzle and wherein the engaging step further comprises:
   securing the bushing to the fitting of the nozzle.

4. The method of using a transparent disk while performing a dental procedure inside a patient's mouth as set forth in claim 3 further comprising the step of:
   inserting the nozzle through the aperture of the disk prior to the securing step.

5. The method of using a transparent disk having an aperture while performing a dental procedure inside a patient's mouth wherein the aperture has an insert therein comprising the steps of:
   inserting a dental instrument through the aperture;
   frictionally engaging the insert with the instrument; and
   blocking with the disk matter ejected from the patient's mouth during the dental procedure.

6. The method of using a transparent disk while performing a dental procedure inside a patient's mouth as set forth in claim 5 wherein the insert has a central bore and wherein the frictionally engaging step further comprises:
   frictionally engaging the bore of the insert with the instrument.

7. The method of using a transparent disk while performing a dental procedure inside a patient's mouth as set forth in claim 6 further comprising the step of:
   inserting the nozzle through the aperture of the disk prior to the frictionally engaging step.

* * * * *